(12) United States Patent
Lee et al.

(10) Patent No.: US 11,510,571 B2
(45) Date of Patent: Nov. 29, 2022

(54) BODY TEMPERATURE SENSOR MODULE TO BE ATTACHED TO SKIN, COMPRISING INTELLIGENT SEMICONDUCTOR

(71) Applicants: 3A LOGICS INC., Seongnam-si (KR); AMOTECH CO., LTD., Incheon (KR)

(72) Inventors: Pyeong Han Lee, Seongnam-si (KR); Kwang Beom Park, Seoul (KR); Sung Wan Kim, Gwangju-si (KR); Hyoung Jun Kim, Yongin-si (KR); Sang Min Yoon, Seoul (KR); Beom Jin Kim, Bucheon-si (KR); Hyung Il Baek, Yongin-si (KR); Kyung Hyun Ryu, Seoul (KR); Jae Il Park, Yeoju-si (KR); Eul Young Jung, Incheon (KR); Chan Woo Lee, Suwon-si (KR)

(73) Assignees: AMOTECH CO., LTD., Incheon (KR); 3A LOGICS INC., Incheon (KR)

( * ) Notice: Subject to any disclaimer, the term of this patent is extended or adjusted under 35 U.S.C. 154(b) by 416 days.

(21) Appl. No.: 16/644,325

(22) PCT Filed: Sep. 13, 2018

(86) PCT No.: PCT/KR2018/010767
§ 371 (c)(1),
(2) Date: Mar. 4, 2020

(87) PCT Pub. No.: WO2019/054776
PCT Pub. Date: Mar. 21, 2019

(65) Prior Publication Data
US 2020/0205662 A1  Jul. 2, 2020

(30) Foreign Application Priority Data
Sep. 15, 2017  (KR) .................. 10-2017-0118752

(51) Int. Cl.
*A61B 5/00* (2006.01)
*A61B 5/01* (2006.01)
(Continued)

(52) U.S. Cl.
CPC ............ *A61B 5/0008* (2013.01); *A61B 5/002* (2013.01); *A61B 5/01* (2013.01); *A61B 5/6832* (2013.01);
(Continued)

(58) Field of Classification Search
CPC ......... A61B 5/0008; A61B 5/002; A61B 5/01; A61B 5/6832; A61B 2560/0209;
(Continued)

(56) References Cited

U.S. PATENT DOCUMENTS

2014/0288381 A1* 9/2014 Faarbaek ............. A61B 5/0002
600/300
2016/0159667 A1* 6/2016 Hwang ................. C02F 1/4691
156/60

(Continued)

FOREIGN PATENT DOCUMENTS

KR  20150066560  6/2015
KR  20160015419  2/2016
(Continued)

OTHER PUBLICATIONS

International Search Report—PCT/KR2018/010767 dated Jan. 9, 2019.

*Primary Examiner* — Orlando Bousono
(74) *Attorney, Agent, or Firm* — Cantor Colburn LLP (57) ABSTRACT

Provided is a body temperature sensor module to be attached to the skin including: a power supply unit electrically connected to a flexible printed circuit board and providing driving power; a temperature sensor mounted on one surface of the flexible printed circuit board and measuring the body (Continued)

temperature of the wearer; a communication module for transmitting information measured by the temperature sensor to an external communication module; a control unit for controlling the driving of the power supply unit, the temperature sensor and the communication module; a protection member for preventing the exposure of the flexible printed circuit board, the power supply unit, the temperature sensor, the communication module and the control unit to the outside; and a membrane layer separably attached to one surface of the protection member, and formed from a nanofiber web having micropores to be able to block moisture and allow the passage of air.

18 Claims, 5 Drawing Sheets

(51) Int. Cl.
| | | |
|---|---|---|
| *A61M 35/00* | (2006.01) | |
| *H04Q 9/00* | (2006.01) | |
| *H04W 12/06* | (2021.01) | |
| *H04W 52/02* | (2009.01) | |

(52) U.S. Cl.
CPC .............. *A61M 35/00* (2013.01); *H04Q 9/00* (2013.01); *H04W 12/06* (2013.01); *H04W 52/0229* (2013.01); *A61B 2560/0209* (2013.01); *A61B 2560/0214* (2013.01); *A61B 2562/0271* (2013.01); *A61B 2562/164* (2013.01); *A61B 2562/166* (2013.01); *A61B 2562/18* (2013.01); *H04Q 2209/43* (2013.01)

(58) Field of Classification Search
CPC .... A61B 2560/0214; A61B 2562/0271; A61B 2562/164; A61B 2562/166; A61B 2562/18; A61M 35/00; H04Q 9/00; H04Q 2209/43; H04W 12/06; H04W 52/0229
See application file for complete search history.

(56) References Cited

U.S. PATENT DOCUMENTS

| | | | |
|---|---|---|---|
| 2016/0228823 A1* | 8/2016 | Seo | B01D 15/363 |
| 2017/0011210 A1* | 1/2017 | Cheong | A61B 5/681 |
| 2017/0291143 A1* | 10/2017 | Zhou | B01D 61/36 |
| 2018/0028069 A1* | 2/2018 | Shi | G01K 1/14 |

FOREIGN PATENT DOCUMENTS

| | | |
|---|---|---|
| KR | 20170024544 | 3/2017 |
| KR | 20170031547 | 3/2017 |
| WO | 2017014380 | 1/2017 |

* cited by examiner

BODY TEMPERATURE SENSOR MODULE TO BE ATTACHED TO SKIN, COMPRISING INTELLIGENT SEMICONDUCTOR

CROSS-REFERENCE TO RELATED APPLICATIONS

This application is a national entry of PCT Application No. PCT/KR2018/010767 filed on Sep. 13, 2018, which claims priority to and the benefit of Korean Application No. 10-2017-0118752 filed on Sep. 15, 2017, in the Korean Patent Office, the entire contents of which are incorporated herein by reference.

TECHNICAL FIELD

The present invention relates to a body temperature sensor module to be attached to skin, and more specifically, to a body temperature sensor module to be attached to skin that is capable of obtaining biological information of a wearer and transmitting the obtained information in a state in which the body temperature sensor module is attached to a wearer's body.

BACKGROUND ART

A body temperature and a heartbeat are simply measured using a contact type thermometer or non-contact type thermometer. General thermometers include mercury sensors, alcohol sensors, infrared sensors, and the like.

Such a thermometer can measure a body temperature and a heartbeat of a wearer when a predetermined time period elapses in a state in which the thermometer is put on or is in contact with a body of the wearer.

Accordingly, since a state in which the thermometer is put on a patient who is an infant or young child or a patient for whom moving is uncomfortable should be maintained to measure a body temperature and a heartbeat of the patient, another person's help is required. Accordingly, there is a problem of a task of measuring the temperature and the heartbeat of the patient who is the infant or young child or the patient for whom moving is uncomfortable being very cumbersome.

In addition, in order to measure a body temperature using a conventional thermometer, a state in which the thermometer is in contact with a body of a target person is maintained for a predetermined time period, and the thermometer is separated from the wearer to check the body temperature from the thermometer. Accordingly, there is a problem of a task of checking a body temperature in real time or periodically using the conventional thermometer being very cumbersome.

DISCLOSURE

Technical Problem

The present invention is directed to providing a body temperature sensor module to be attached to skin that is capable of simply being attached to a body of a wearer and monitoring a body temperature of the wearer in real time.

In addition, the present invention is also directed to providing a body temperature sensor module to be attached to skin that is capable of recharging a battery.

In addition, the present invention is also directed to providing a body temperature sensor module to be attached to skin that is capable of securing air permeability while blocking an effective ingredient from passing through.

Technical Solution

One aspect of the present invention provides a body temperature sensor module to be attached to skin, the body temperature sensor module including a power supply unit electrically connected to a flexible printed circuit board and configured to supply driving power, a temperature sensor mounted on one surface of the flexible printed circuit board and configured to measure a body temperature of a wearer, at least one communication module through which information measured by the temperature sensor is transmitted to an external communication module, a control unit configured to control driving of the power supply unit, the temperature sensor, and the communication module, a protection member configured to prevent the flexible printed circuit board, the power supply unit, the temperature sensor, the communication module, and the control unit from being exposed to the outside, and a membrane layer detachably attached to one surface of the protection member and formed of a nanofiber web having micro-pores to block moisture and allow air to pass through the membrane layer.

According to the exemplary embodiment of the present invention, the control unit may receive power from the power supply unit using a wake-up function of the at least one communication module, and in a case in which the power is supplied to the control unit, the at least one communication module may be pairing with the external communication module.

In this case, the at least one communication module may include a first communication module through which authentication is performed with the external communication module, and a second communication module through which the information measured by the temperature sensor is transmitted.

As an example, the first communication module may be a near field communication (NFC) antenna module, and the second communication module may be a Bluetooth antenna module.

In addition, the protection member may include an exposing hole formed in a region corresponding to the temperature sensor to pass through the protection member, and the temperature sensor may be disposed in the exposing hole. In this case, the exposing hole may be filled with a sealing member, and the sealing member may block external moisture from moving to the flexible printed circuit board.

The flexible printed circuit board may include a cut portion having a predetermined area and formed to be cut inward, and the power supply unit may be disposed in the cut portion. As an example, the power supply unit may be a plate-shaped flexible battery or a paper battery.

The body temperature sensor module may include a wireless power receiving antenna patterned and formed on one surface of the flexible printed circuit board to recharge the power supply unit.

The protection member may be formed of a material having flexibility.

In addition, the membrane layer may be attached to skin of the wearer by an ampoule including a mixing ingredient, a drying ingredient, a viscosity control ingredient, and a moisture retaining ingredient.

As an example, the ampoule may be a mixed liquid in which water, alcohol, polymer, and oil are mixed at a predetermined ratio, and the ampoule may further include a functional material.

In addition, the membrane layer may serve as a protective layer configured to protect the ampoule by being attached to the skin of the wearer.

As another example, the membrane layer may be formed to have a stack structure including a shape retaining layer formed of a nanofiber web in which nanofibers including a synthetic polymer are accumulated and stacked on one surface of the protection member, and a liquid medicine layer formed of a nanofiber web in which nanofibers including a functional material and a water-soluble polymer are accumulated and stacked on one surface of the shape retaining layer.

In addition, the functional material may include a dry storage material which is difficult to store in a liquid state.

The shape retaining layer may be a nanofiber web in which a spinning solution in which a synthetic polymer and a solvent are mixed is electrospun and accumulated to have micro-pores, and the liquid medicine layer may be a nanofiber web, in which a spinning solution in which a water-soluble polymer, a functional material, and a solvent are mixed, is electrospun and accumulated to have micro-pores.

The functional material may be a mixture having at least one ingredients among an ingredient to aid in skin whitening, an ingredient to help reduce skin wrinkles, an ingredient to help block ultraviolet rays, an antioxidant ingredient, a skin and hair conditioning ingredient, and an antimicrobial ingredient.

A release film may be attached to an exposed surface of the membrane layer.

Advantageous Effects

According to the present invention, in a state in which a body temperature sensor module to be attached to skin is attached to a body of a wearer, information about a body temperature of the wearer can be obtained through a temperature sensor, and the information about the obtained body temperature can be transmitted to the outside through a communication module, and thus a body temperature state of the wearer can be checked and monitored in real time.

Since supplying of power is started in a case in which the wearer is authenticated through the communication module, a physical driving button can be omitted, and thus the body temperature sensor module can be realized to have a thin shape.

An embedded battery can be recharged, and a membrane layer can be separated from the body temperature sensor module, and thus the body temperature sensor module can be repeatedly reused.

Since the membrane layer attached to skin can block an effective ingredient from passing through the membrane layer and also secure air permeability, a beneficial effect can be maximized due to the effective ingredient, and a side effect such as skin troubles can also be prevented.

MODES OF THE INVENTION

Hereinafter, embodiments that are easily performed by those skilled in the art will be described in detail with reference to the accompanying drawings. The embodiments of the present invention may be implemented in several different forms and are not limited to the embodiments described herein. Parts irrelevant to description are omitted in the drawings in order to clearly explain the embodiments of the present invention. Similar parts are denoted by similar reference numerals throughout this specification.

Figure 1:
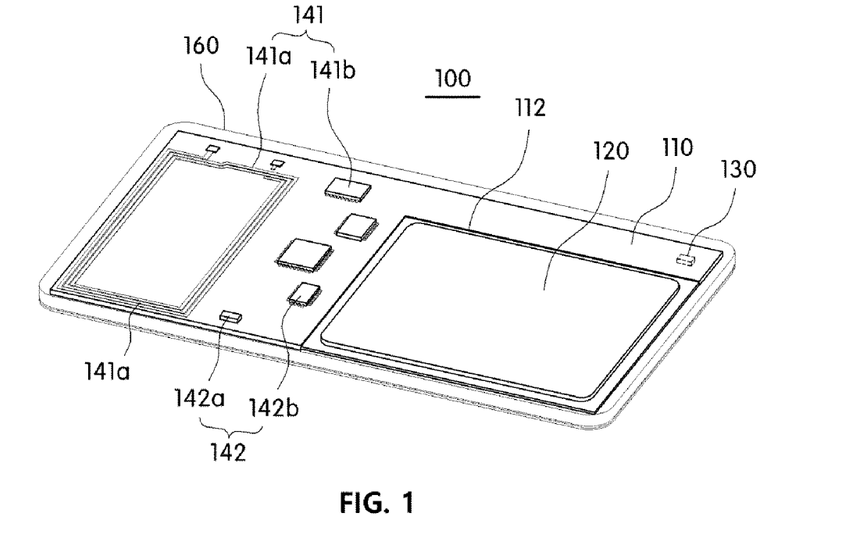
FIG. 1 is a schematic view illustrating a body temperature sensor module to be attached to skin according to one embodiment of the present invention.
Figure 7:
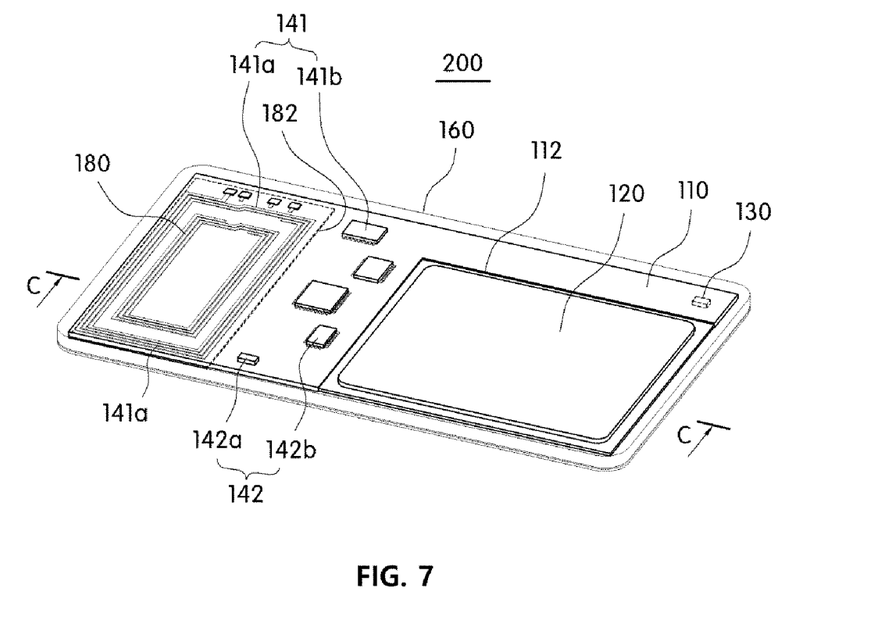
FIG. 7 is a schematic view illustrating a body temperature sensor module to be attached to skin according to another embodiment of the present invention.

As illustrated in FIGS. 1 and 7, a body temperature sensor module 100 or 200 to be attached to skin according to one embodiment of the present invention includes a flexible printed circuit board (FPCB) 110, a power supply unit 120, a temperature sensor 130, at least one communication modules 141 and 142, a control unit 150, a protection member 160, and a membrane layer 170 or 170'.

The FPCB 110 may be a basic material on which various circuit elements or circuit patterns are mounted. The FPCB 110 may be a well-known FPCB having flexibility and using polyimide (PI), polyethylene terephthalate (PET), or the like, and the circuit elements may be chip set type elements configured to serve predetermined functions.

In this case, the FPCB 110 may include a cut portion 112 having a predetermined area and formed to be cut inward. In this case, the power supply unit 120 may be disposed in the cut portion 112. As an example, the cut portion 112 may be formed to be cut inward from any one corner of four corners of the FPCB 110.

Accordingly, in a case in which the power supply unit 120 is disposed in the cut portion 112, a part or an entire thickness of the power supply unit 120 may be accommodated in the cut portion 112. Accordingly, the body temperature sensor module 100 or 200 to be attached to skin may be formed in a thin film form.

The power supply unit 120 may provide driving power required for driving the circuit elements mounted on the FPCB 110. To this end, the power supply unit 120 may be electrically connected to the FPCB 110.

Although the power supply unit 120 may be stacked on one surface of the FPCB 110, the power supply unit 120 may be disposed in the cut portion 112 to reduce the total thickness as described above and may be electrically connected to the FPCB 110.

As an example, although the power supply unit 120 may be a well-known coin battery or rectangular battery, the power supply unit 120 may be a plate-shaped flexible battery to reduce a weight and volume thereof and also to have a high capacity. As a specific example, the power supply unit 120 may be a well-known paper battery or pouch type battery.

That is, the body temperature sensor module 100 or 200 to be attached to skin according to the present invention can secure a sufficient charging capacity, reduce a total weight, and have a thin film form because the power supply unit 120 is formed as the plate-shaped flexible battery.

In this case, although the power supply unit 120 may be a primary battery, the power supply unit 120 may be a secondary battery capable of being reused. In addition, in the case in which the power supply unit 120 is the secondary battery, the power supply unit 120 may be recharged through a wireless power transmission method.

As an example, as illustrated in FIG. 7, the body temperature sensor module 200 to be attached to skin according to one embodiment of the present invention may include a wireless power receiving antenna 180, and the wireless power receiving antenna 180 may be an antenna pattern formed on one surface of the FPCB 110 to have a predetermined pattern.

Accordingly, the body temperature sensor module 200 to be attached to skin may receive wireless power transmitted from an external charger through the wireless power receiving antenna 180 and recharge the power supply unit 120 with the received wireless power. In this case, the wireless charging method may be any one of a well-known magnetic induction method, a magnetic resonance method, or an ultrasonic method.

The wireless power receiving antenna 180 may be directly formed on one surface of the FPCB 110 through a printing method using a conductor.

In this case, the FPCB 110 may include a wireless charging circuit (not shown) for recharging power of the power supply unit 120 with power received through the wireless power receiving antenna 180. In addition, the FPCB 110 may further include a protection circuit for preventing overcharging of the power supply unit 120 when the power supply unit 120 is charged. The wireless charging circuit and the protection circuit may be controlled through driving of the control unit 150.

Accordingly, in the body temperature sensor module 200 to be attached to skin according to one embodiment of the present invention, the power of the power supply unit 120 can be recharged through the wireless method, and stable driving power can be secured. In addition, in the body temperature sensor module 200 to be attached to skin according to one embodiment of the present invention, even when the power of the power supply unit 120 is discharged completely, the power supply unit 120 can be recharged, and thus the power supply unit 120 can be reused without being replaced.

Figure 8:
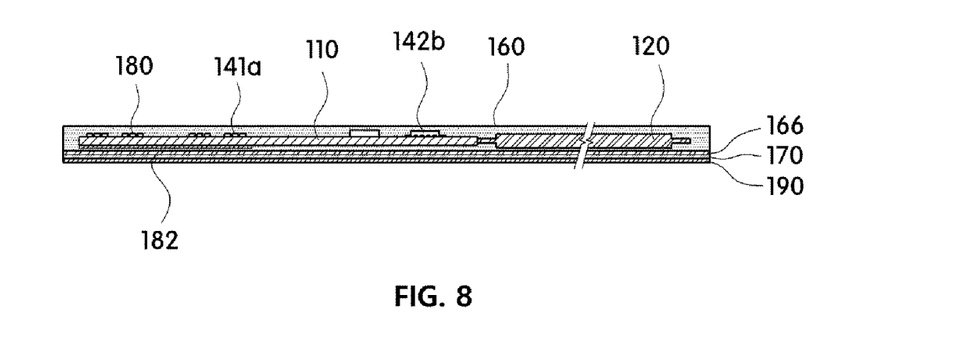
FIG. 8 is a cross-sectional view taken along line C-C of FIG. 7.

Meanwhile, in the case in which the body temperature sensor module 200 to be attached to skin according to one embodiment of the present invention includes the wireless power receiving antenna 180, as illustrated in FIG. 8, the body temperature sensor module 200 to be attached to skin may include a well-known shield sheet 182 disposed at a region corresponding to the wireless power receiving antenna 180. The shield sheet 182 may shield a magnetic field generated from the wireless power receiving antenna 180 and focus the magnetic field in a required direction to improve wireless charging efficiency.

In this case, any well-known magnetic material, such as a ferrite, amorphous, or polymer material which is used in a shield sheet, may be used in the shield sheet. In addition, the shield sheet may also be formed to be separated into a plurality of fine pieces through flake processing to secure flexibility.

The temperature sensor 130 may be mounted on one surface of the FPCB 110 and detect a body temperature of a wearer.

Specifically, the temperature sensor 130 may be mounted on a bottom surface of both surfaces of the FPCB 110. Accordingly, in a case in which the body temperature sensor module 100 or 200 to be attached to skin according to one embodiment of the present invention is attached to a body of the wearer, the temperature sensor 130 may be easily exposed to the body of the wearer.

Figure 2:
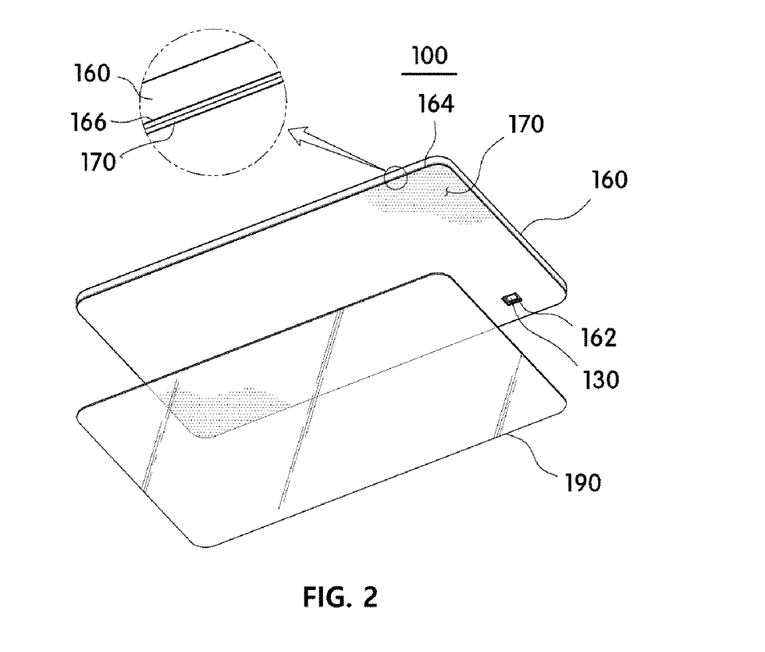
FIG. 2 is a bottom view illustrating a state in which a release film is separated from FIG. 1.
Figure 3:
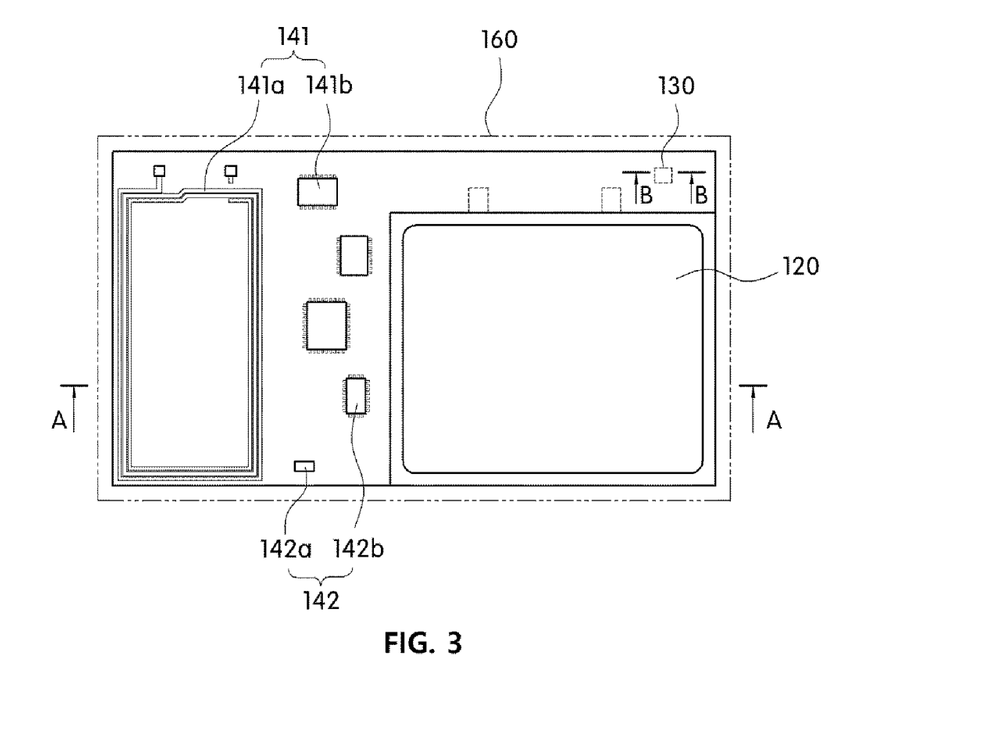
FIG. 3 is a plan view of FIG. 1.
Figure 4:
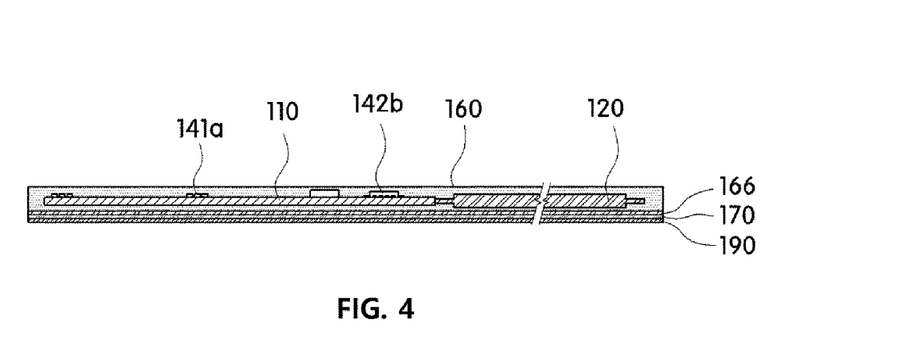
FIG. 4 is a cross-sectional view taken along line A-A of FIG. 3.

To this end, as illustrated in FIG. 2, an exposing hole 162 may be formed in a region, which corresponds to the temperature sensor 130, of the protection member 160 to pass through the protection member 160. Accordingly, in a case in which the body temperature sensor module 100 or 200 to be attached to skin according to the present invention is attached to skin of the wearer, the temperature sensor 130 may face the skin of the wearer through the exposing hole 162 and easily measure a body temperature of the wearer.

In this case, the temperature sensor 130 may be driven by driving of the control unit 150, and information about the body temperature detected by the temperature sensor 130 may be transmitted to an external device through the communication module 142. In addition, the body temperature may be measured using the temperature sensor 130 periodically or consecutively.

Figure 5:
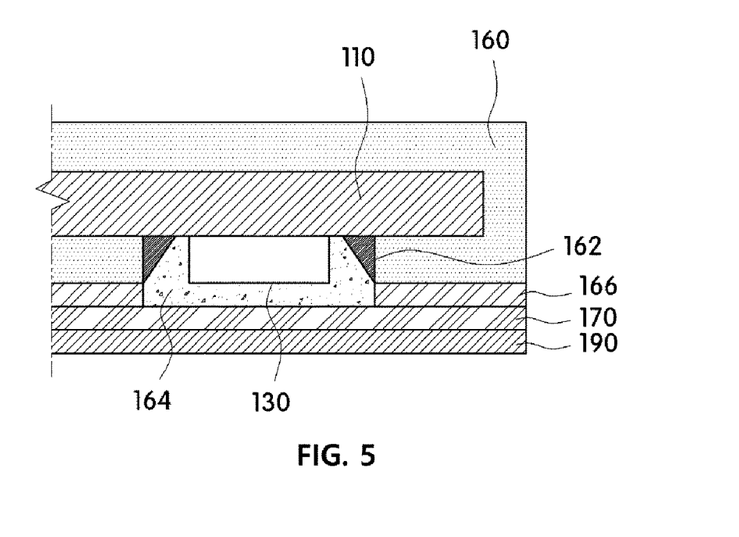
FIG. 5 is a cross-sectional view taken along line B-B of FIG. 3.

In this case, as illustrated in FIG. 5, the exposing hole 162 may be filled with a sealing member 164 to prevent moisture from being introduced into a side of the FPCB 110. The sealing member 164 may fill a gap between the exposing hole 162 and the temperature sensor 130 along an edge of the exposing hole 162 or may fill the exposing hole 162 to completely cover the temperature sensor 130.

The at least one communication modules 141 and 142 may be mounted on the FPCB 110, and the at least one communication modules 141 and 142 may be transmitted information measured by the temperature sensor 130 to an external communication module.

In this case, the at least one communication modules 141 and 142 may serve to provide data measured by the temperature sensor 130 to an external electronic device and serve as a switch to allow power of the power supply unit 120 to be supplied to the control unit 150 through a wake-up function.

That is, in the body temperature sensor module 100 or 200 to be attached to skin according to one embodiment of the present invention, in a case in which the wearer is authenticated through the communication module 141, the power of the power supply unit 120 may be supplied to the control unit 150. Accordingly, in the body temperature sensor module 100 or 200 to be attached to skin according to one embodiment of the present invention, a physical switch or button which needs manipulation of the wearer can be omitted.

Accordingly, since the body temperature sensor module 100 or 200 to be attached to skin according to one embodiment of the present invention does not need an on or off operation for driving, the physical switch or on and off buttons can be omitted. Accordingly, in the body temperature sensor module 100 or 200 to be attached to skin according to one embodiment of the present invention, since a structure of the product can be simplified and the physical on and off buttons are omitted, the product can be further thinned.

To this end, the at least one communication modules 141 and 142 may include a first communication module 141 for authentication with the external electronic device and a second communication module 142 for transmission of information measured by the temperature sensor 130 through pairing with an external communication module included in the external electronic device.

According to the present invention, the external electronic device may be a portable electronic device such as a smartphone or a tablet personal computer (PC), a server, or a medical device. In addition, the external electronic device may be a device in which a communication module corresponding to at least one of the first communication module 141 and the second communication module 142 is embedded.

As a specific example, the first communication module 141 may be a near field communication (NFC) antenna module, and the second communication module 142 may be a Bluetooth antenna module. In addition, the external electronic device may be a smartphone in which an NFC antenna module and a Bluetooth antenna module are embedded.

To this end, an NFC antenna 141a may be formed into a pattern on one surface of the FPCB 110, and a Bluetooth antenna 142a may be mounted on the FPCB 110 to be positioned outside the NFC antenna 141a. In addition, the FPCB 110 may include driving chips 141b and 142b to drive the NFC antenna 141a and the Bluetooth antenna 142a.

Accordingly, in a case in which the body temperature sensor module 100 or 200 to be attached to skin according to one embodiment of the present invention is close to the external electronic device, the wearer may be authenticated through the NFC antenna 141a. In addition, in a case in which the wearer is authenticated through the NFC antenna 141a, since power is supplied to the Bluetooth antenna module by the power supply unit 120, the Bluetooth antenna module may be pairing with a Bluetooth antenna module included in the smartphone.

Accordingly, data measured by the temperature sensor 130 may be transmitted to the smartphone pairing through the second communication module 142, and the wearer may check the data measured by the temperature sensor 130 through the smartphone in real time.

In this case, the data transmitted to the smartphone may be stored in the smartphone or separately stored in a server or another electronic device using a network connected to the smartphone.

According to the present invention, the NFC antenna module has been described as an example of the first communication module 141 for authentication of the wearer, but the present invention is not limited thereto, and any well-known short range wireless communication method, such as a radio frequency identification (RFID) communication method, an infrared data association (IrDA) communication method, an ultra-wideband (UWB) communication method, ZigBee communication method, long range (LoRa) communication method, a radio detecting and ranging (RADAR) communication method, a low power wireless communication method, or a Wi-Fi communication method, may be used, and the FPCB 110 may include a chipset suitable for an applied communication method.

In addition, the first communication module 141 may also be a wide area communication module for performing wireless communication according to a communication method including spatial modulation (SM), a general packet radio service (GPRS), enhanced data rates for global system for mobile communications (GSM) evolution (EDGE), LTE-Advanced (LTE-A), long term evolution (LTE), code-division multiple access (CDMA), wideband CDMA (WCDMA), evolution-data optimized (EVDO), a wireless broadband (WiBro), or mobile worldwide interoperability for microwave access (WiMax).

Figure 6:
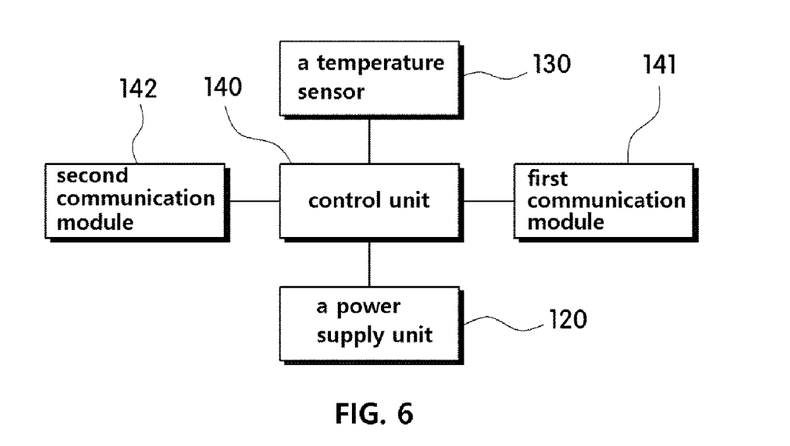
FIG. 6 is a block diagram illustrating relationships between a control unit and other components of the body temperature sensor module to be attached to skin according to the present invention.

The control unit 150 may generate effective information based on a signal detected by the temperature sensor 130 and a control command to transmit the generated information to the outside and control general driving of the body temperature sensor module 100 or 200 to be attached to skin.

To this end, the control unit 150 may include at least one circuit element mounted on one surface of the FPCB 110.

As an example, the circuit element may be a chipset such as a microcontroller unit (MCU) capable of generating data based on a signal measured by the temperature sensor 130 and transmitting the data to the outside.

As described above, the body temperature sensor module 100 or 200 to be attached to skin according to one embodiment of the present invention may transmit a body temperature of the wearer, which is measured by the temperature sensor 130, to a server or electronic device close to or away from the body temperature sensor module 100 or 200 through the second communication module 142.

Accordingly, the server or electronic device may store the data transmitted from the second communication module 142 and update information of the body temperature of the wearer to accumulate the information of the body temperature of the wearer in real time or periodically.

Accordingly, the data stored in the server or electronic device can be monitored in real time, or the date accumulated in the server or electronic device can be used to analyze and apply the information of the body temperature of the wearer to manage a health state of the wearer.

In addition, in a case in which the wearer is a person such as a patient or aged person whose body temperature needs to be monitored in real time or periodically, the wearer can be monitored in real time or periodically using the information of the body temperature of the wearer transmitted to the server or electronic device, and prompt aid can be provided in an emergency situation.

As described above, the body temperature sensor module 100 or 200 to be attached to skin according to one embodiment of the present invention may be applied in a healthcare system, a silver industry, and medical industry fields.

Meanwhile, the body temperature sensor module 100 or 200 to be attached to skin according to one embodiment of the present invention may include the protection member 160 for preventing the circuit patterns and the circuit elements or the power supply unit 120 mounted on the FPCB 110 from being exposed to the outside.

The protection member 160 may be formed of a material having flexibility so that flexibility can be secured in the body temperature sensor module 100 or 200 to be attached to skin according to one embodiment of the present invention.

Accordingly, even when the body temperature sensor module 100 or 200 to be attached to skin according to one embodiment of the present invention is attached to a curved portion of the body of the wearer, a state in which the body temperature sensor module 100 or 200 to be attached to the skin is pressed against the body of the wearer can be continuously maintained.

To this end, the protection member 160 may be a fluoride polymer resin such as PET, polypropylene (PP), or polyethylene (PE), a sheet such as a release paper, or a molded member formed of a resin material including silicone or polyurethane. However, a material of the protection member 160 is not limited thereto, and any material having flexibility may be used as the material.

The membrane layer 170 or 170' may be attached to one surface of the protection member 160 by an adhesive member 166. The membrane layer 170 or 170' may be directly attached to the skin of the wearer when the body temperature sensor module 100 or 200 to be attached to skin according to one embodiment of the present invention is used.

In this case, the membrane layer 170 or 170' may have a property of blocking moisture and a property of air permeability. That is, the membrane layer 170 or 170' may be formed of a nanofiber web having micro-pores so that moisture may be blocked but air may pass through the membrane layer 170 or 170'. As a non-restrictive example, an average diameter of the micro-pores may be 10 µm or less.

Accordingly, the membrane layer 170 or 170' may expedite permeation of an effective ingredient such as a functional material into skin due to the property of blocking moisture and may also supply air to the skin due to the air permeability. Accordingly, even when the body temperature sensor module 100 or 200 to be attached to skin according to one embodiment of the present invention is attached to the wearer for a long time period, the wearer can be protected from a side effect such as skin problems.

In this case, the adhesive member 166 may be a non-board type member such as a tackifier or adhesive or may be a board type member in which the tackifier or adhesive is applied to both surfaces of a board, such as double sided tape. Preferably, the adhesive member 166 may be a detachable member so that the body temperature sensor module 100 or 200 to be attached to skin according to one embodiment of the present invention is reusable.

In addition, the membrane layer 170 or 170' may completely cover one surface of the protection member 160, or a portion corresponding to the exposing hole 162 may be formed to be open so that the temperature sensor 130 is exposed to the outside.

In this case, the membrane layer 170 may be attached to a body portion of the wearer by an ampoule applied to the skin of the wearer.

Accordingly, the membrane layer 170 may protect the ampoule applied to the skin of the wearer or expedite permeation of an effective ingredient beneficial to skin into the skin of the wearer.

In this case, the ampoule may be a mixed liquid in which a mixing ingredient, a drying ingredient, a viscosity control ingredient, and a moisture retaining ingredient are mixed at a predetermined ratio. As an example, the ampoule may be a mixed liquid in which water that is the mixing ingredient, alcohol that is the drying ingredient, polymer that is the viscosity control ingredient, and oil that is the moisture retaining ingredient are properly mixed at a predetermined ratio.

That is, a total drying time period of the body temperature sensor module 100 or 200 to be attached to skin, which is attached to the skin, can be controlled by the ampoule in which percentages of the mixing ingredient, the drying ingredient, the viscosity control ingredient, and the moisture retaining ingredient are properly adjusted according to a purpose of use.

In this case, the ampoule may further include a functional material in addition to the four main ingredients, and a role and a function of the membrane layer 170 or 170' may be changed according to whether the functional material is included in the materials of the ampoule.

As an example, in the case in which the ampoule includes the functional material, the membrane layer 170 may cover and protect the ampoule. In this case, the membrane layer 170 may serve as a protective layer such that the functional material included in the ampoule easily permeates into the skin of the wearer.

In addition, in a case in which the membrane layer 170' includes a liquid medicine layer 172 including a functional material, the membrane layer 170' may serve as a source which supplies the functional material to the skin of the wearer. In this case, the ampoule may not include the functional material and may serve as a solvent to dissolve the liquid medicine layer 172. A detailed description thereof will be described below.

According to the present invention, the functional material is a material for skin beauty and wound care and may be a mixture including at least one among an ingredient to aid in skin whitening (arbutin, niacinamide, or ascoglucoside), an ingredient to help reduce skin wrinkles (retinol or adenosine), an ingredient to help block ultraviolet rays (titanium dioxide), an ingredient to help retain moisture and skin elasticity (snail mucus filtrate, acetylhexapeptide, red ginseng collagen, aqua ceramide, regenerated peptide, or galatomyces fermentation broth), a growth factor such as an epidermal growth factor (EGF) or fibroblast growth factor (FGF), protein for therapy, or an antimicrobial substance such as a silver nanomaterial or chitosan.

In addition, the functional material may also be a mixture including at least one selected from among water soluble collagen, vegetable platinum, tocopherol, xylitol, and a vegetable extract.

In this case, the membrane layer 170 or 170' may serve as the protective layer which simply covers the skin of the wearer or may both serve as the protective layer which covers the skin of the wearer and serve to supply an effective ingredient to the skin of the wearer.

Figure 9:
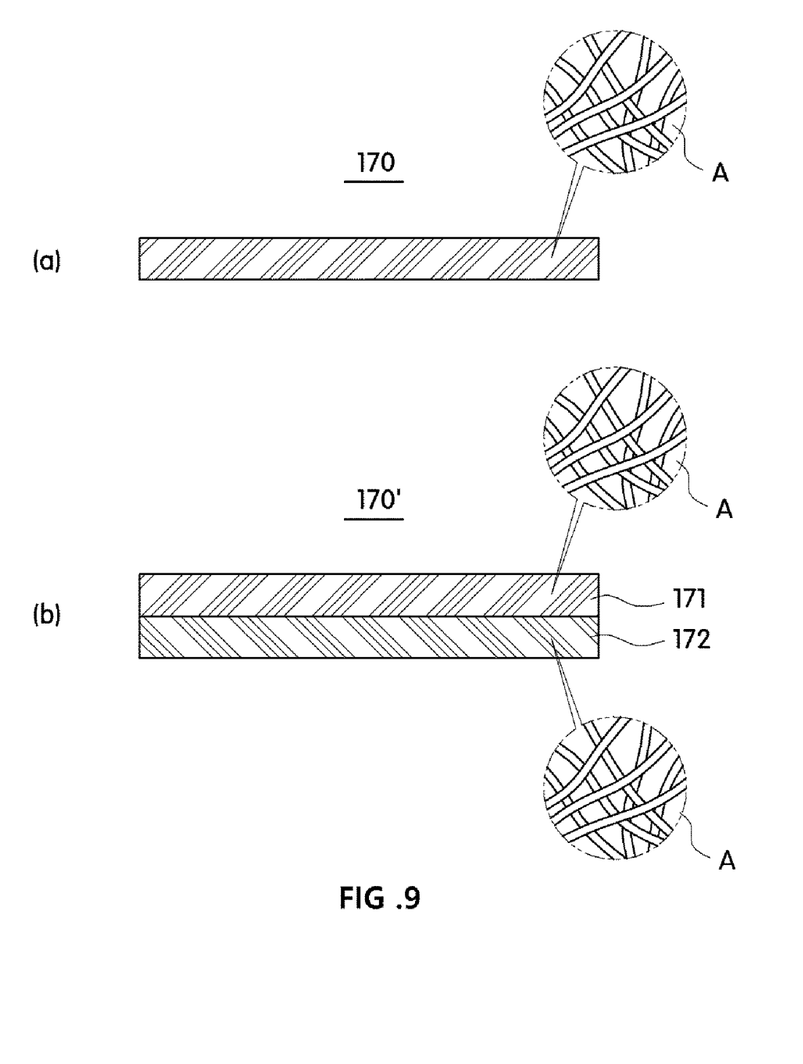
FIG. 9 is a cross-sectional view illustrating a detailed structure of a membrane layer applicable to the body temperature sensor module to be attached to skin according to the present invention.

Specifically, as illustrated in FIG. 9A, in the body temperature sensor module 100 or 200 to be attached to skin according to the present invention, the membrane layer 170 may be the nanofiber web having a single layer in which a spinning solution in which a synthetic polymer and a solvent are mixed is electrospun and accumulated to have the micro-pores. In this case, the solvent may be water or alcohol or may also be an organic solvent other than water or alcohol.

In this case, the synthetic polymer may be fiber forming polymer which is not dissolved by the solvent but is electrospinnable to form the nanofiber web through the electrospinning. Accordingly, even when the membrane layer 170 is in contact with the solvent included in the effective ingredient such as a liquid medicine or the ampoule applied to the skin of the wearer, the membrane layer 170 may not be dissolved by the solvent and may maintain a form of the nanofiber web.

Accordingly, in a state in which the ampoule including the effective ingredient is applied to the skin of the wearer, one surface of the membrane layer 170 is attached to the body portion to which the ampoule is applied to cover the body portion, and the membrane layer 170 may protect the ampoule applied to the body portion.

In this case, since the membrane layer 170 is formed of the synthetic polymer which is not dissolved by the solvent, the membrane layer 170 can be attached to the skin for a long time period in a state in which the form of the nanofiber web is maintained.

In addition, the membrane layer 170 may prevent the effective ingredient included in the ampoule from passing through the membrane layer 170 and moving to the protection member 160. Accordingly, the effective ingredient can be effectively absorbed in the body of the wearer due to the membrane layer 170.

The synthetic polymer is not specifically limited when the synthetic polymer is a resin which is capable of being dissolved by the solvent for electrospinning and capable of forming the nanofiber by electrospinning and capable of being not dissolved by the solvent. As a non-restrictive example, the synthetic polymer may be polyvinylidene fluoride (PVdF), poly(vinylidene fluoride-co-hexafluoropropylene), perfuluropolymer, polyvinylchloride, polyvinylidene chloride or copolymers thereof, polyethylene glycol dialkyl ethers and a polyethylene glycol derivative including polyethylene glycol dialkyl ester, poly(oxymethylene-oligo-oxyethylene), polyoxide including polyethylene oxide and polypropylene oxide, polyvinylacetate, poly(vinylpyrrolidone-vinylacetate), polystyrene and polystyrene acrylonitrile copolymers, polyacrylonitrile (PAN), polyacrylonitrile copolymers including polyacrylonitrile methyl methacrylate copolymers including acrylate copolymers, polymethylmethacrylate, polymethylmethacrylate copolymers, or a mixture thereof.

As another example, as illustrated in FIG. 9B, in the body temperature sensor module 100 or 200 to be attached to skin according to one embodiment of the present invention, the membrane layer 170' may include a shape retaining layer 171 and the liquid medicine layer 172.

In this case, the shape retaining layer 171 may be formed of a synthetic polymer material capable of being electrospun, and the liquid medicine layer 172 may be formed of a water-soluble polymer which is water-soluble and electrospinnable and a functional material.

Specifically, the shape retaining layer 171 may be a nanofiber web formed by mixing an electrospinnable synthetic polymer and a solvent at a proper ratio to prepare a spinning solution and by electrospinning the spinning solution to have micro-pores.

In this case, the synthetic polymer may be a fiber forming polymer which is not dissolved by the solvent but is electrospinnable to be formed as the nanofiber web having the micro-pores through electrospinning. Accordingly, even when the water-soluble liquid medicine layer 172 is in contact with the ampoule applied to the skin of the wearer and is released in a liquid or gel state, the shape retaining layer 171 may not be dissolved by the solvent included in the ampoule and may maintain the form of the nanofiber web. Accordingly, the shape retaining layer 171 may serve to protect the released liquid medicine layer 172.

Accordingly, even when the liquid medicine layer 172 is released due to contact with the solvent, the membrane layer 170' may maintain a state in which the membrane layer 170' is attached to the skin due to the shape retaining layer 171.

In addition, in a case in which the liquid medicine layer 172 is released by the solvent, the shape retaining layer 171 may absorb a water-soluble polymer material forming the liquid medicine layer 172 through the micro-pores. Accordingly, the shape retaining layer 171 may serve as a moisture retaining layer which retains moisture.

In this case, the shape retaining layer 171 is not dissolved by the ampoule applied to the skin of the wearer and may be formed of a material which is the same as that of the above described membrane layer 170.

In addition, the liquid medicine layer 172 may be a nanofiber web formed by mixing a water-soluble polymer, a functional material, and a solvent at an appropriate ratio to prepare a spinning solution and by electrospinning the spinning solution to have micro-pores.

That is, the liquid medicine layer 172 may be formed of the spinning solution in which the water-soluble polymer material and the functional material are mixed. Accordingly, when the liquid medicine layer 172 is in contact with the ampoule applied to the skin of the wearer, the liquid medicine layer 172 may be changed to a release state, the functional material may be absorbed in the skin, and the water-soluble polymer material may be absorbed in the shape retaining layer 171.

In this case, the water-soluble polymer material is not specifically limited when the water-soluble polymer material is a polymer material which is soluble in water or alcohol and electrospinnable to form a nanofiber through electrospinning. As a non-restrictive example, the water-soluble polymer material may be a mixture including at least one selected among polyvinyl alcohol (PVA), polyvinyl pyrrolidone (PVP), polyethylene oxide (PEO), carboxyl methyl cellulose (CMC), starch, polyacrylic acid (PAA), and hyaluronic acid.

In addition, in the present embodiment, the ampoule may include the functional material, but the ampoule which does not include a functional material may be used due to the liquid medicine layer 172 including the functional material.

Meanwhile, the functional material included in the liquid medicine layer 172 may be a dry storage material which is difficult to store in a liquid state. The dry storage material may be released in a liquid or gel state when the water-soluble polymer is dissolved. Accordingly, the dry storage material released in the liquid or gel state may be smoothly absorbed in the skin of the wearer.

As an example, the dry storage material may be a vitamin, enzyme, protein, a peptide-vitamin C derivative, or the like. Generally, the above described dry storage materials have a property of only dissolving in a liquid state. However, it is difficult to store the dry storage material for a long time period in the liquid state.

According to the present invention, the dry storage material, which is difficult to store in the liquid state, is included in the spinning solution together with the water-soluble polymer material and the solvent, the spinning solution including the dry storage material is electro spun to form nanofiber so as to form the liquid medicine layer 172 having a form of the nanofiber web, and thus the dry storage material may be restricted in the nanofibers forming the liquid medicine layer 172 in a dried state.

Accordingly, the dry storage material, which is difficult to store in a liquid state, can be stored for a long time period, and in a case in which the water-soluble polymer is dissolved by the solvent, the functional material in a dried state is released together with the water-soluble polymer and transmitted to the skin and thus smoothly permeates into the skin.

That is, when the body temperature sensor module 100 or 200 to be attached to skin according to the present invention is attached to the skin, the water-soluble polymer forming the liquid medicine layer 172 is dissolved by the solvent, and the functional material restricted in the water-soluble polymer may be released. Accordingly, the released functional material may be absorbed in the skin, and the water-soluble polymer dissolved by the solvent may be absorbed in the shape retaining layer 171.

In addition, the spinning solution forming the liquid medicine layer 172 may also include oil at a predetermined ratio to appropriately control a time period for which the liquid medicine layer 172 is dissolved when the liquid medicine layer 172 is in contact with the solvent. Accordingly, since a total drying time period for which the membrane layer 170' attached to the skin of the wearer is dried is controlled, a drying time period suitable for a purpose of use, such as for sleeping, pack, and protection, can be realized.

Meanwhile, the body temperature sensor module 100 or 200 to be attached to skin according to the present invention may include a release film 190 attached to one surface of the membrane layer 170 or 170'. The release film 190 may prevent the membrane layer 170 or 170' from being exposed to the outside.

As an example, the release film 190 may be a fluoride polymer resin such as PET, PP, and PE, or a release paper.

While the specific embodiments of the present invention have been described, the scope of the present invention is not limited to the suggested embodiments, and other embodiments may be easily suggested by those skilled in the art by adding, modifying, and deleting other components in the same scope of the present invention, and these may also be within the scope of the present invention.

The invention claimed is:

1. A body temperature sensor module to be attached to skin, comprising:
    a power supply unit electrically connected to a flexible printed circuit board and configured to supply driving power;
    a temperature sensor mounted on one surface of the flexible printed circuit board and configured to measure a body temperature of a wearer;
    at least one communication module through which information measured by the temperature sensor is transmitted to an external communication module;
    a control unit configured to control driving of the power supply unit, the temperature sensor, and the communication module;
    a protection member configured to prevent the flexible printed circuit board, the power supply unit, the temperature sensor, the communication module, and the control unit from being exposed to the outside; and
    a membrane layer detachably attached to one surface of the protection member and formed of a nanofiber web having micro-pores to block moisture and allow air to pass through the membrane layer,
    wherein the membrane layer is formed to have a stack structure including:
    a shape retaining layer formed of a nanofiber web in which nanofibers including a synthetic polymer are accumulated and stacked on one surface of the protection member; and
    a liquid medicine layer formed of a nanofiber web in which nanofibers including a functional material and a water-soluble polymer are accumulated and stacked on one surface of the shape retaining layer.

2. The body temperature sensor module of claim 1, wherein:
    the control unit receives power from the power supply unit using a wake-up function of the at least one communication module; and
    in a case in which the power is supplied to the control unit, the at least one communication module is pairing with the external communication module.

3. The body temperature sensor module of claim 2, wherein the at least one communication module includes:
    a first communication module through which authentication is performed with the external communication module; and
    a second communication module through which the information measured by the temperature sensor is transmitted.

4. The body temperature sensor module of claim 3, wherein:
    the first communication module is a near field communication (NFC) antenna module; and
    the second communication module is a Bluetooth antenna module.

5. The body temperature sensor module of claim 1, wherein:
    the protection member includes an exposing hole formed in a region corresponding to the temperature sensor to pass through the protection member; and
    the temperature sensor is disposed in the exposing hole.

6. The body temperature sensor module of claim 5, further comprising a sealing member which fills the exposing hole,
    wherein the sealing member blocks external moisture from moving to the flexible printed circuit board.

7. The body temperature sensor module of claim 1, wherein:
    the flexible printed circuit board includes a cut portion having a predetermined area and formed to be cut inward; and
    the power supply unit is disposed in the cut portion.

8. The body temperature sensor module of claim 1, wherein the power supply unit includes a plate-shaped flexible battery.

9. The body temperature sensor module of claim 1, further comprising a wireless power receiving antenna patterned and formed on one surface of the flexible printed circuit board to recharge the power supply unit.

10. The body temperature sensor module of claim 1, wherein the protection member is formed of a material having flexibility.

11. The body temperature sensor module of claim 1, wherein the functional material includes a dry storage material which is difficult to store in a liquid state.

12. The body temperature sensor module of claim 1, wherein:
    the shape retaining layer is a nanofiber web in which a spinning solution in which a synthetic polymer and a solvent are mixed is electrospun and accumulated to have micropores; and
    the liquid medicine layer is a nanofiber web, in which a spinning solution in which a water-soluble polymer, a functional material, and a solvent are mixed, is electrospun and accumulated to have micropores.

13. The body temperature sensor module of claim 1, wherein a release film is attached to an exposed surface of the membrane layer.

14. A body temperature sensor module to be attached to skin, comprising:
    a power supply unit electrically connected to a flexible printed circuit board and configured to supply driving power;
    a temperature sensor mounted on one surface of the flexible printed circuit board and configured to measure a body temperature of a wearer;
    at least one communication module through which information measured by the temperature sensor is transmitted to an external communication module;
    a control unit configured to control driving of the power supply unit, the temperature sensor, and the communication module;
    a protection member configured to prevent the flexible printed circuit board, the power supply unit, the temperature sensor, the communication module, and the control unit from being exposed to the outside; and a membrane layer detachably attached to one surface of the protection member and formed of a nanofiber web having micro-pores to block moisture and allow air to pass through the membrane layer wherein the membrane layer is capable of being attached to skin of the wearer by an ampoule including a mixing ingredient, a drying ingredient, a viscosity control ingredient, and a moisture retaining ingredient.

15. The body temperature sensor module of claim 14, wherein the ampoule is a mixed liquid in which water, alcohol, polymer, and oil are mixed at a predetermined ratio.

16. The body temperature sensor module of claim 14, wherein the ampoule further includes a functional material.

17. The body temperature sensor module of claim 14, wherein the membrane layer serves as a protective layer configured to protect the ampoule by being attached to the skin of the wearer.

18. The body temperature sensor module of claim 16, wherein the functional material includes a mixture having at least one ingredients among an ingredient to aid in skin whitening, an ingredient to help reduce skin wrinkles, an ingredient to help block ultraviolet rays, an antioxidant ingredient, a skin and hair conditioning ingredient, and an antimicrobial ingredient.

* * * * *